US012440636B2

(12) United States Patent
Lilly et al.

(10) Patent No.: US 12,440,636 B2
(45) Date of Patent: Oct. 14, 2025

(54) REUSABLE FACE MASK FOR CANNULAS

(71) Applicant: di Ciao, LLC, Florence, SC (US)

(72) Inventors: Terry W. Lilly, Florence, SC (US); Laura Bruno Lilly, Florence, SC (US); Michelle Lilly Solorio, Lansing, MI (US)

(73) Assignee: di Ciao, LLC, Florence, SC (US)

( * ) Notice: Subject to any disclaimer, the term of this patent is extended or adjusted under 35 U.S.C. 154(b) by 622 days.

(21) Appl. No.: 17/962,609

(22) Filed: Oct. 10, 2022

(65) Prior Publication Data

US 2024/0115828 A1 Apr. 11, 2024

(51) Int. Cl.
*A61M 16/06* (2006.01)
*A41D 13/11* (2006.01)

(52) U.S. Cl.
CPC ..... *A61M 16/0672* (2014.02); *A41D 13/1107* (2013.01); *A41D 13/1184* (2013.01); *A41D 2500/20* (2013.01)

(58) Field of Classification Search
CPC ........... A61M 16/0666–0677; A61M 16/0683; A62B 9/04; A62B 9/06; A62B 17/04; A62B 18/02; A62B 18/025; A62B 23/02; A62B 23/025; A61F 9/029
See application file for complete search history.

(56) References Cited

U.S. PATENT DOCUMENTS 4,454,880 A * 6/1984 Muto ................ A61M 16/0683 128/207.18
5,005,571 A * 4/1991 Dietz .................... A61M 16/06 128/207.18
5,839,432 A * 11/1998 Daneshvar ............... A42C 5/04 2/205
6,698,427 B1 3/2004 Clowers
6,805,123 B2 10/2004 Seo
7,255,107 B1 * 8/2007 Gomez ............. A61M 16/0666 128/207.18
10,478,580 B2 11/2019 Klenner et al.
10,556,080 B2 2/2020 Henry et al.
10,632,275 B2 4/2020 Wong et al.
10,980,964 B2 4/2021 Lee et al.
11,284,654 B2 3/2022 Plank et al.
11,324,974 B2 5/2022 Hubbard et al.
11,331,449 B2 5/2022 McLaren et al.
11,344,753 B2 5/2022 Wang
2006/0054169 A1 * 3/2006 Han .................. A61M 16/0683 128/207.18
2007/0044802 A1 * 3/2007 Horne .................. A62B 18/025 128/206.19
2007/0095348 A1 5/2007 Fisher et al.
2008/0110463 A1 5/2008 Hajigato et al.
2015/0273170 A1 10/2015 Bachelder et al.
2015/0289573 A1 10/2015 Haas
2016/0367842 A1 12/2016 Koehler
2017/0208876 A1 7/2017 Al Malki
2018/0008848 A1 1/2018 Moulton et al.
(Continued)

FOREIGN PATENT DOCUMENTS

WO 2011026515 A1 3/2011
WO 2015017647 A2 2/2015

*Primary Examiner* — Valerie L Woodward
(74) *Attorney, Agent, or Firm* — Thrive IP

(57) ABSTRACT

A reusable mask system includes a cannula support assemblage for cannulas with a swivel shield insertable between layers of a mask.

20 Claims, 15 Drawing Sheets

(56) References Cited

U.S. PATENT DOCUMENTS

| | | | |
|---|---|---|---|
| 2021/0368874 | A1 | 12/2021 | Eldibany |
| 2021/0370003 | A1 | 12/2021 | Ronayne et al. |
| 2022/0152332 | A1 | 5/2022 | Collins et al. |

* cited by examiner

REUSABLE FACE MASK FOR CANNULAS

BACKGROUND OF THE DISCLOSURE

People requiring supplemental oxygen ($O_2$) often use an oxygen delivery system consisting of cannula tubing with prongs inserted into nostrils. While $O_2$ cannulas are designed to be soft and lightweight, if a mask must be worn over an $O_2$ cannula to protect the patient, for instance, from airborne contamination or viruses, the mask can adversely affect the fit and comfort of the $O_2$ cannula and can often cause oxygen leakage or restrict oxygen flow. For instance, an N95 mask is designed for a close facial fit around a mouth and nose of a wearer, but the close fit of such masks—while suitable for preventing inhalation of airborne contaminants—can compress lightweight $O_2$ cannula tubing or displace its nose prongs thereby restricting or inhibiting oxygen flow.

A disposable mask is a looser fitting mask than N95 masks. However, a loose mask does not form tight seals around a mouth and nose of the wearer, and therefore, loose masks allow greater unfiltered airflow to occur since the poorer fit may offer less filtration of small airborne particulates. Moreover, regardless of whether tighter or looser fitting masks are worn by persons using $O_2$ cannulas, most masks are intended for a single use. Therefore, each time a new mask is required, the user must reinsert and readjust the $O_2$ cannula to accommodate the new mask, which is not only time-consuming but is likely to result in inconsistent fittings over time.

What is needed in the industry is a reusable face mask that can readily receive an $O_2$ cannula in which the mask and the $O_2$ cannula can be adjusted for a comfortable fit, which will not restrict oxygen flow through the cannula and provide a level of filtration efficiency, not unduly restrict the airflow resistance (breathability), reduce areas of leakage around the mask, and provide the user with a mask that is comfortable to wear.

BRIEF SUMMARY OF THE DISCLOSURE

The present disclosure is directed in general to a reusable face mask system that has embedded receptacles or channels for receiving nasal $O_2$ cannulas. The masks and the cannulas can be adjusted for individual comfort but do not restrict oxygen flow through the cannulas while providing suitable filtration. Further, once the nasal $O_2$ cannula is fitted to the reusable mask, a disposable outer layer mask can be used, or not, with the reusable mask. The reusable masks are simple to make, easy to utilize and can be intermittently removed, washed, and reused.

In an exemplary embodiment, a reusable mask system may include a swivable shield having a first side with a first swivel depending therefrom and a second side with a second swivel depending therefrom; a mask having an external layer and an internal layer forming a pocket therebetween, the swivable shield being insertable in the pocket; a cannula support assemblage having a first assemblage end and a second assemblage end and further including a ventilation director and a nose cradle depending from the ventilation director, the nose cradle being configured for supporting a cannula; a first clip attachable to the first assemblage end and configured to receive the first swivel of the swivable shield; and a second clip attachable to the second assemblage end and configured to receive the second swivel of the swivable shield. The swivable shield in this embodiment may be made of a synthetic resin, and the internal layer may be made of woven fabric.

Also in this embodiment, the first clip and the second clip may be horizontally adjustable, and the ventilation director may be spaced apart from the internal layer and configured to deflect exhalations away from the cannula.

Still further, this embodiment may include a cannula support positioned at a first assemblage end or a second assemblage end for supporting a portion of the cannula, and a nose segment may be provided that is connectable to one of the cannula support assemblage or the mask, the nose segment configured to provide a nose cushion.

The reusable mask system may further include a nose bridge that can be connected to the cannula support assemblage or to the mask in order to fit the cannula support assemblage or the mask to a user. The nose bridge may be malleable for customizing user fitment and receivers may be located in the pocket to receive respective clips.

In another embodiment, a reusable mask system may include a shield having a swivel depending therefrom; a mask having an external layer and an internal layer forming a pocket therebetween, the shield being insertable in the pocket; a cannula support top disposed on the mask, the cannula support top being configured to support a portion of a cannula; and a clip attachable to the cannula support top configured to receive the swivel. The cannula support top may include an assemblage end and a shoulder support extending from the assemblage end for supporting another portion of the cannula, and the clip may be horizontally adjustable. Receivers may be positioned in the pocket to receive respective clips.

Also in this reusable mask system, a ventilation deflector may be provided that is placed apart from the internal layer and can deflect exhalations away from the cannula. Still further, a nose cradle may extend from the cannula support top and may support other parts or portions of the cannula.

A cushioning nose segment may also be provided in this embodiment to connect to the cannula support top or to the mask. And a nose bridge may be connected to the cannula support assemblage or to the mask to fit the cannula support assemblage or the mask to a user. The nose bridge may be malleable for customized user fitment.

In yet another embodiment, a reusable mask system may include a swivelable facial shield and a cannula support assemblage disposed proximate the shield, the cannula support assemblage having a first end and a second end with a first shoulder support depending from the first end and a second shoulder support depending from the second end, and further including a ventilation director and a nose cradle depending from the ventilation director, the first and second shoulder supports and the nose cradle being configured for supporting a cannula.

The reusable mask system may also include a mask with an external layer and an internal layer forming a pocket therebetween in which the shield is insertable in the pocket. Still further, receivers may be positioned in the pocket to receive the shield.

Additional objects and advantages of the present subject matter are set forth in, or will be apparent to, those of ordinary skill in the art from the description herein. Also, it should be further appreciated that modifications and variations to the specifically illustrated, referenced, and discussed features, processes, and elements hereof may be practiced in various embodiments and uses of the disclosure without departing from the spirit and scope of the subject matter. Variations may include, but are not limited to, substitution of equivalent means, features, or steps for those illustrated, referenced, or discussed, and the functional, operational, or positional reversal of various parts, features, steps, or the like. Those of ordinary skill in the art will better appreciate the features and aspects of the various embodiments, and others, upon review of the remainder of the specification.

BRIEF DESCRIPTION OF THE DRAWINGS

A full and enabling disclosure of the present subject matter, including the best mode thereof directed to one of ordinary skill in the art, is set forth in the specification, which refers to the appended figures, wherein.

DETAILED DESCRIPTION OF THE DISCLOSURE

Figure 1:
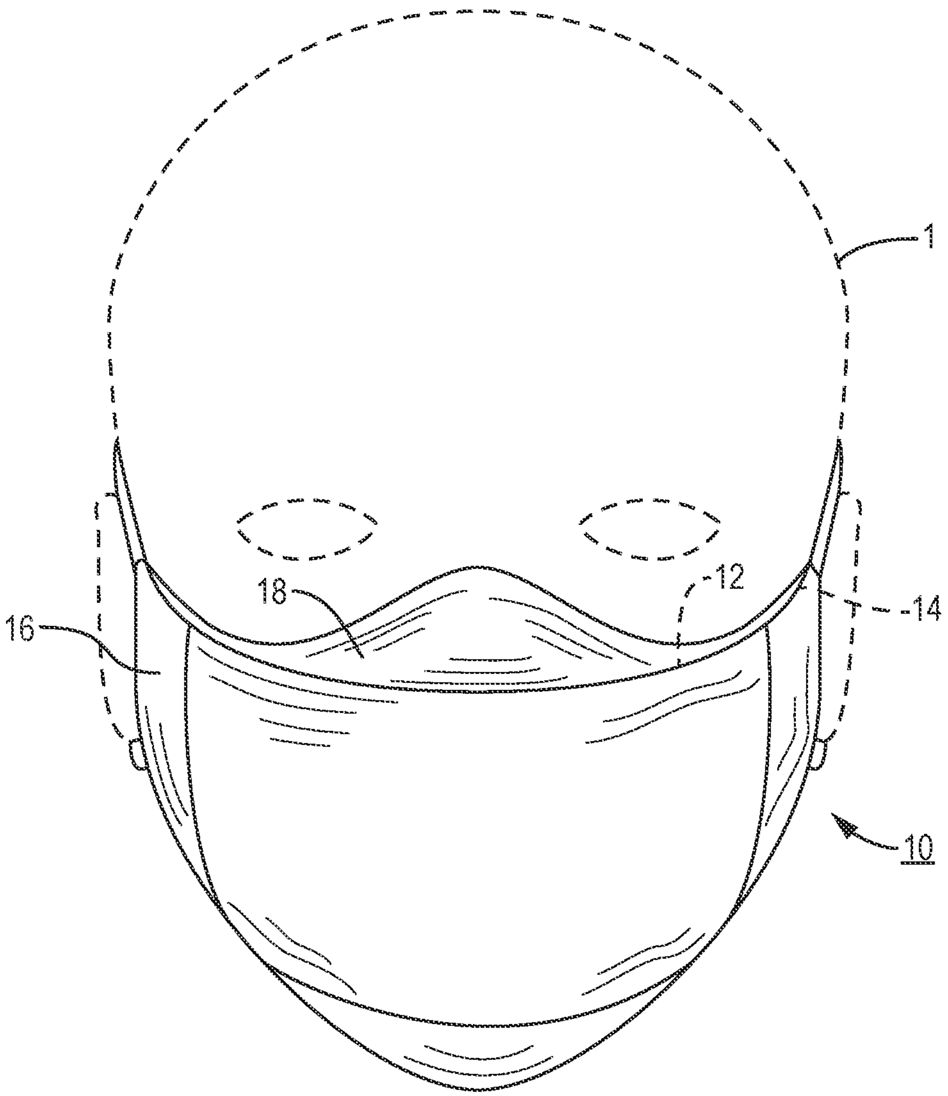
FIG. 1 is a front view of a mask system according to an aspect of the disclosure shown in intended use.

As required, detailed embodiments are disclosed herein; however, the disclosed embodiments are merely exemplary and may be embodied in various forms. Therefore, specific structural and functional details disclosed herein are not to be interpreted as limiting, but merely as a basis for the claims and as a representative basis for teaching one skilled in the art to variously employ the exemplary embodiments of the present disclosure, as well as their equivalents.

Unless defined otherwise, all technical and scientific terms used herein have the same meaning as is commonly understood by one of ordinary skill in the art to which this disclosure belongs. In the event that there is a plurality of definitions for a term or acronym herein, those in this section prevail unless stated otherwise.

Wherever the phrase "for example," "such as," "including," and the like are used herein, the phrase "and without limitation" is understood to follow unless explicitly stated otherwise. Similarly, "an example," "exemplary" and the like are understood to be non-limiting.

The term "substantially" allows for deviations from the descriptor that do not negatively impact the intended purpose. Descriptive terms are understood to be modified by the term "substantially" even if the word "substantially" is not explicitly recited.

The term "about" when used in connection with a numerical value refers to the actual given value, and to the approximation to such given value that would reasonably be inferred by one of ordinary skill in the art, including approximations due to the experimental and or measurement conditions for such given value.

The terms "comprising" and "including" and "having" and "involving" (and similarly "comprises," "includes," "has," and "involves") and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, et cetera. Thus, for example, "a device having components a, b, and c" means that the device includes at least components a, b, and c. Similarly, the phrase "a method involving steps a, b, and c" means that the method includes at least steps a, b, and c.

Where a list of alternative component terms is used, e.g., "a structure such as 'a', 'b', 'c', 'd' or the like", or 'a' or 'b'," such lists and alternative terms provide meaning and context unless indicated otherwise.

Unless the context clearly requires otherwise, throughout the description and the claims, the words "comprise," "comprising," and the like are to be construed in an inclusive sense as opposed to an exclusive or exhaustive sense; in the sense of "including, but not limited to."

The various embodiments of the disclosure and/or equivalents falling within the scope of present disclosure overcome or ameliorate at least one of the disadvantages of the prior art or provide a useful alternative.

Detailed reference will now be made to the drawings in which examples embodying the present subject matter are shown. The detailed description uses numerical and letter designations to refer to features of the drawings. The drawings and detailed description provide a full and written description of the present subject matter, and of the manner and process of making and using various exemplary embodiments, so as to enable one skilled in the pertinent art to make and use them, as well as the best mode of carrying out the exemplary embodiments. The drawings are not necessarily to scale, and some features may be exaggerated to show details of particular components. Thus, the examples set forth in the drawings and detailed descriptions are provided by way of explanation only and are not meant as limitations of the disclosure. The present subject matter thus includes any modifications and variations of the following examples as come within the scope of the appended claims and their equivalents.

Turning now to FIG. 1, an embodiment of a face mask system according to the disclosure is broadly designated by element number 10 and shown being worn by a user 1. The face mask system 10 generally includes a swivable, reusable mask or shield 12, a cannula support top or assemblage 14, a cloth mask or portion 16, and a nose assemblage 18. As explained in greater detail below, the mask 12 may be constructed from a plastic material and is washable, and therefore, reusable. Moreover, although the reusable mask 12 is shown inserted behind or within layers of the cloth portion 16, the mask 12 can be used without the cloth portion 16.

Figure 2:
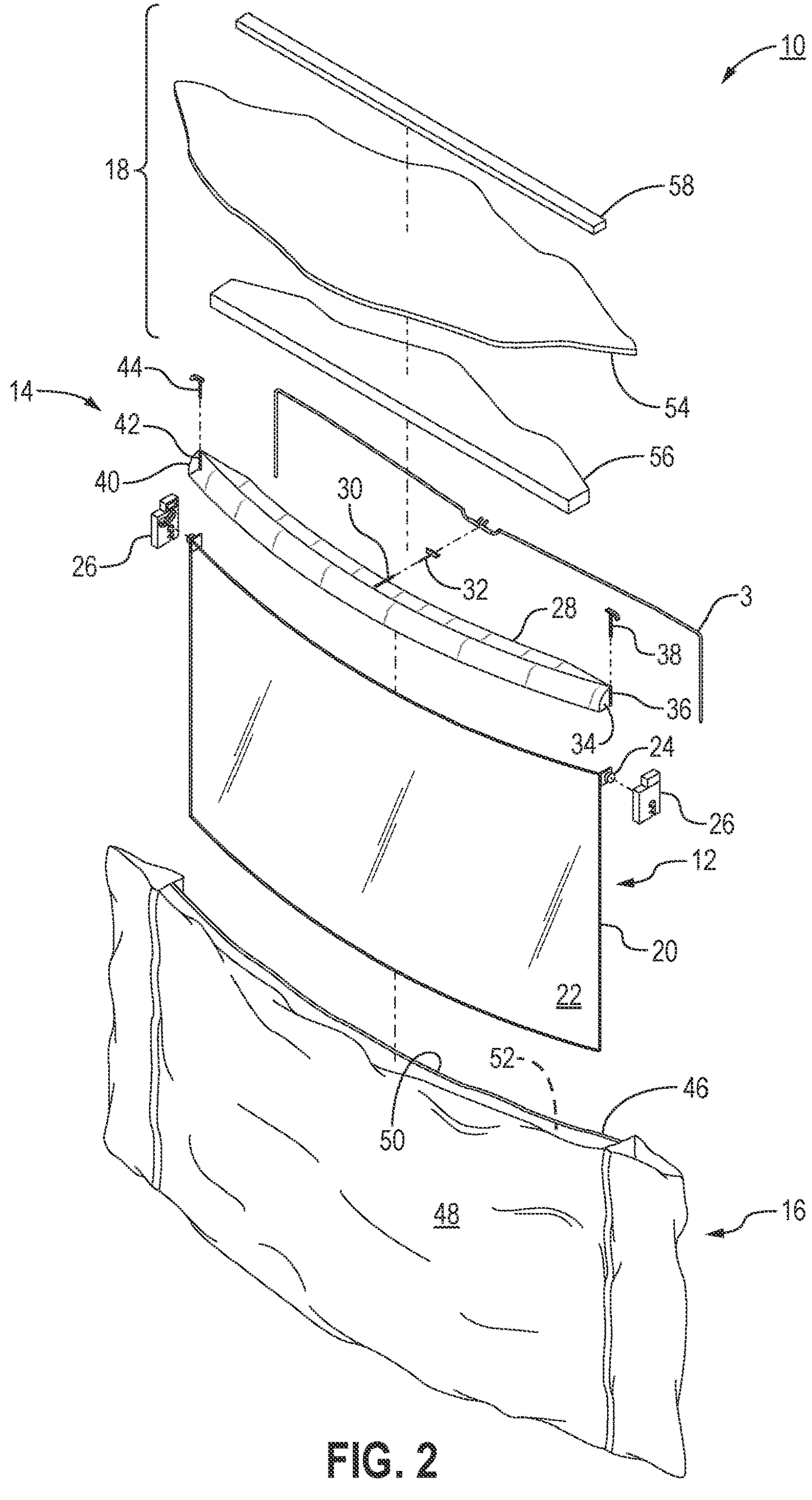
FIG. 2 is an exploded perspective view of the mask system as in FIG. 1.

FIG. 2 is a detailed view of various components of the mask system 10 shown in a disassembled state. Here, the reusable mask 12 briefly introduced above has an inner layer or first or face side 20, and an outer side or external layer 22. In this example, swivels 24 extend from the face-side layer 20 for receiving respective clips 26 that connect the mask 12 to cannula support top 14 as explained by exemplary operation below.

As further shown in FIG. 2, the cannula support top 14 includes a ventilation ridge, deflector, or director 28 to direct exhaled air downward and away from nose and eyes of a user 1 (see FIG. 1). Along a midpoint of the ventilation director 28, a midpoint receiver 30 may be formed to receive a nose cannula cradle or support 32 for supporting part of a cannula 3. Similarly, at a first or left end 34 of the cannula support top 14, a first or left receiver 36 may be provided for receiving a first or left cannula cradle or shoulder support 38 to cradle another portion of the cannula 3. Likewise, at a second or right end 40 of the cannula support top 14, a second or right receiver 42 may be provided for receiving a second or right cannula cradle or shoulder support 44 to cradle yet another part of the cannula 3, which is free of impediments. Exemplary embodiments of the nose cannula cradle 32 and the first and second cannula supports 38, 44 are discussed in further detail below.

Turning to the cloth portion 16 briefly introduced above, the cloth portion 16 may be a single-use disposable mask, or it can be made from various washable materials for reuse. In either case, the materials selected will provide a level of filtration while not unduly restricting airflow resistance (breathability), depending on the level of protection required. In this example, the cloth portion 16 may include a top portion 46, an outer layer 48, and an inner layer 50 with a pocket or sleeve 52 formed between the outer layer 48 and the inner layer 50 for receiving the mask 12, as will be further described below.

The top portion 46, the outer layer 48, and the inner layer 50 of the cloth portion 16 may be made with appropriate material. By way of specific example, the face-side material layer 50 may be a layer of a woven, softer wicking fabric or other washable material and chosen for comfort in addition to providing a level of filtration while not unduly restricting airflow resistance (breathability). In some alternative embodiments, certain layers can be made of non-woven fabric, such as polypropylene, which is usually 20 or 25 grams per square meter (gsm) in density for bacteria filtration and air permeability as used with surgical face masks, or polystyrene, polycarbonate, polyethylene, polyester, and other suitable materials.

FIG. 2 also particularly shows the nose assemblage 18 briefly introduced above, which, in this example, may include a cloth nose portion 54, a contoured nose segment or portion 56, and a nose bridge or clip 58. The nose portion 54 may be formed integrally with the cloth portion 16, or it may be separately attachable. The contoured nose segment 56 may be made of foam and inserted into pockets of the nose portion 54 or otherwise attachable to the nose portion 54 using adhesives, fasteners, slits, and the like. The foam nose segment 56 can be removed and washed or replaced by a user as needed. The foam 56 should be a sufficient length to lay on top of portions of the cannula 3 exiting nostrils to maximize comfort in either direction of ears of the user 1 (see FIG. 1). If the user 1 uses the left cannula cradle 38 and the right cannula support cradle 44 to direct the cannula 3 downwards as an alternative to using ears to support the cannula 3 then the foam nose segment 56 will not lay on top of portions of the cannula 3 but will still provide comfort to the user 1.

The nose clip 58 shown in FIG. 2 may be made from malleable or shapeable metal, which the user 1 can shape to best fit an individual nose (see FIG. 1). The nose clip 58 can be easily removed and is replaceable with a new nose clip or can removed before washing the cloth mask 16. The nose foam 56 and the nose clip 58 can be insertable within the nose portion 54.

Figure 3:
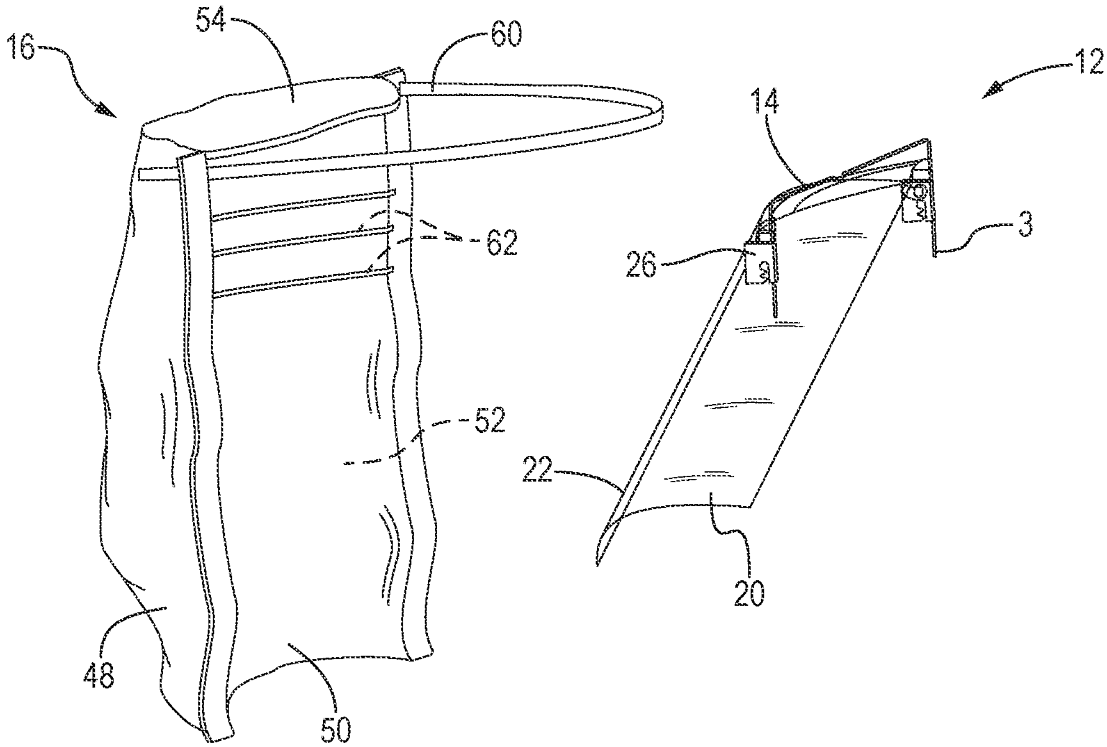
FIG. 3 is a partially exploded, left perspective view of the mask system as in FIG. 2, particularly showing an insertable, reusable mask in a swiveled position relative to a cloth portion.

Turning now to FIG. 3, the face mask system 10 is shown partially disassembled with the reusable mask 12 swiveled approximately thirty degrees (30°) in a direction of the cloth mask 16 with the nose portion 54 attached thereto. Here, the cannula 3 is shown partially disposed along the cannula support top 14 as discussed above with portions of the cannula 3 trailing outside of the clips 26 of the cannula support top 14 and the first side 20 of the mask 12. As shown, the second side 22 of the mask 12 faces the cloth portion 16, which may have a strap or cord 60 attached thereto for holding the mask 12 and the nose portion 54 in place. A gator strap (not shown) may also be attached at or near a lower area of the mask 16 for further security.

Figure 4:
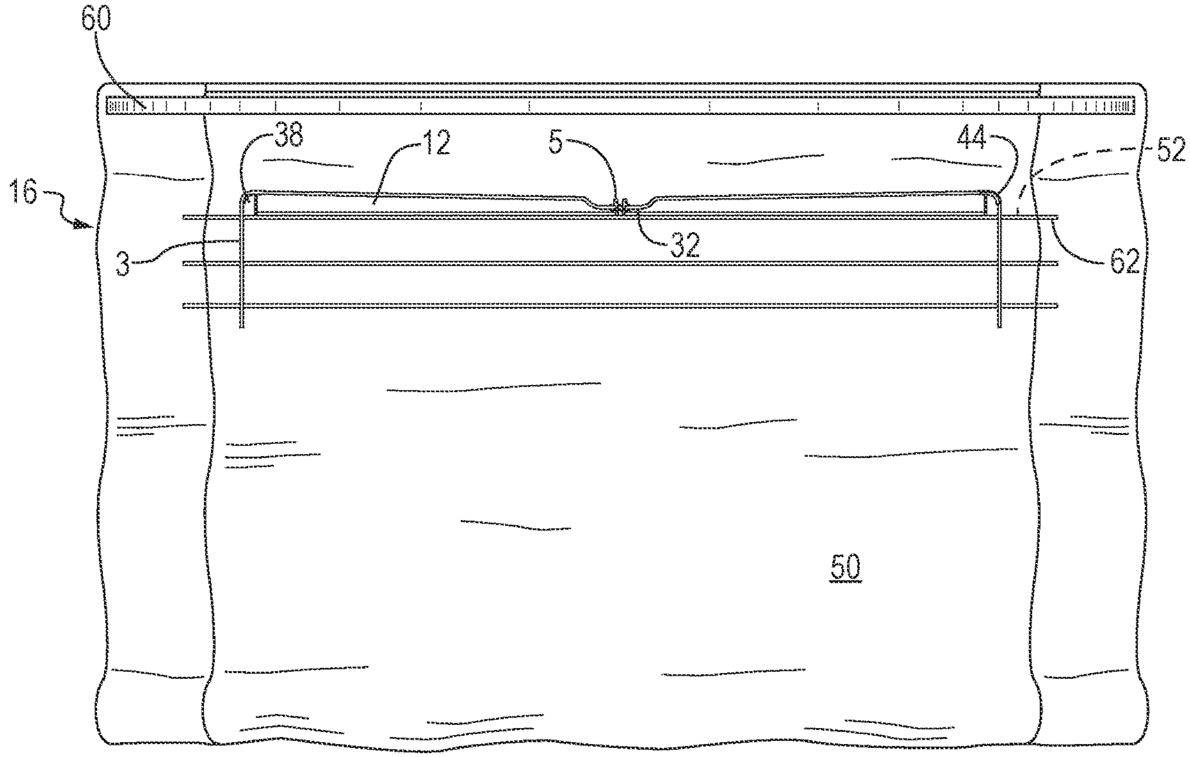
FIG. 4 is a rear elevational view of the reusable mask inserted in the cloth portion as in FIG. 3.

With reference to both FIGS. 3 and 4, slots or slits 62 may be formed across the inner layer 50. The slots 62 open into the pocket 52, which as introduced above, is formed between the outer layer 48 and the inner layer 50 for receiving the mask 12. As will be discussed below in more detail, different slots 62 may be provided to adjust a height or position of the mask 12 relative to the cloth portion 16 to accommodate different user preferences. For example, FIG. 4 shows the mask 12 inserted into the pocket 52 via a topmost slot 62 with portions of the cannula 3 cradled by the nose cannula cradle 32 and the first and second cannula supports 38, 44.

Figure 5:
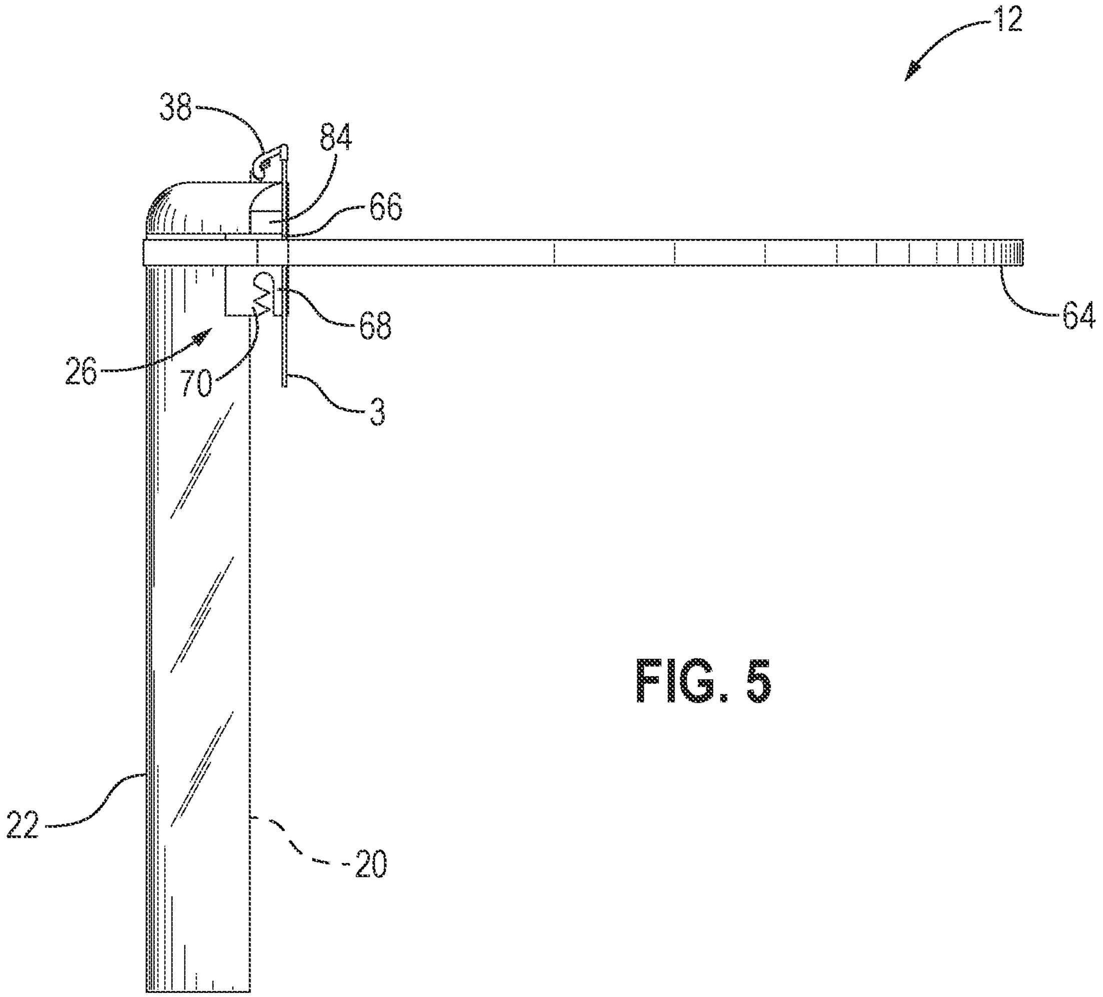
FIG. 5 is a left side elevational view of the insertable, reusable mask as in FIG. 3 without the cloth portion.
Figure 6:
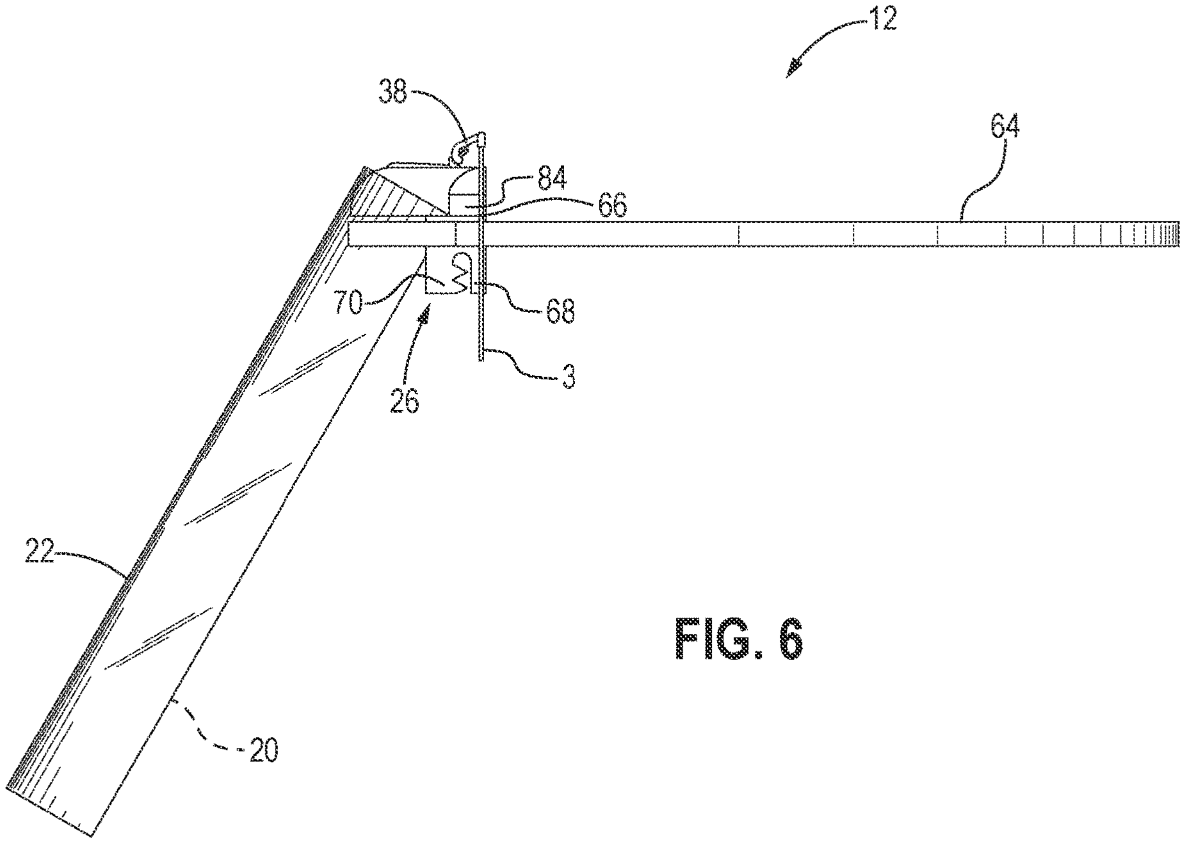
FIG. 6 is similar to FIG. 5 but showing the reusable mask in a swiveled position.
Figure 7:
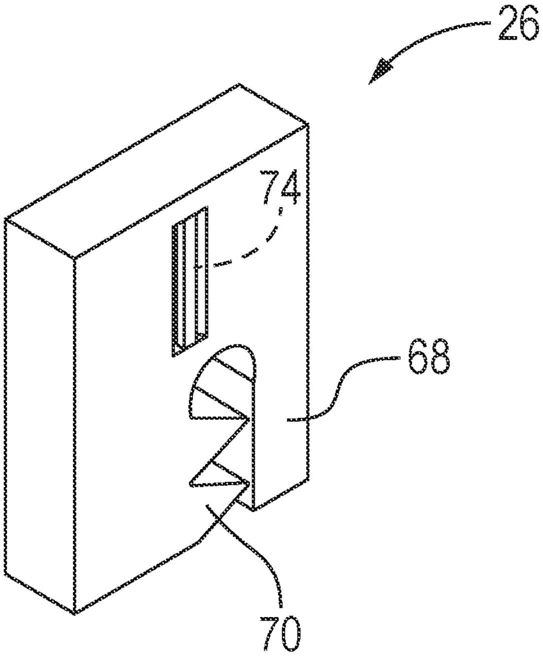
FIG. 7 is a detailed perspective view of an exemplary clip as may be used in the embodiment of FIG. 3, particularly showing a receiving aperture for a strap and insertion components for connection to the cloth portion.

By way of further example, FIGS. 5 and 6 most clearly shows left side views of the mask 12 with a portion of the cannula 3 extending from the second cannula supports 38 in a direction of the inner side 20 of the mask 12. FIG. 6 particularly shows the front side 22 of the mask 12 swiveled forward, which may be necessary for a user to ingest medicine or food and liquids. As shown in these figures, height adjustability of the mask 12 is effected in part by inserting insertion arms 68 and teeth 70 of the clips 26 into receivers 86, which will be discussed with reference to FIG. 12, infra. Similarly, horizontal adjustability of the mask 12 can effected by adjusting the tops 66 of the clips 26 relative to respective spacers 84 of the cannula support top 14, which will be discussed with reference to FIGS. 14 and 15, infra. Finally, in this example, a separate cord or strap 64 may be used with the mask 12 or cannula support top 14, which can be used without the cloth portion 16. Compare strap 60 in FIG. 3. In this regard, FIG. 7 shows a variation of the clip 26 in which a receiving aperture and detent or pawl 74 may be provided for receiving the strap 60 to allow a user to pull and tighten (or loosen) the strap 60 via the detent 74.

Figure 8:
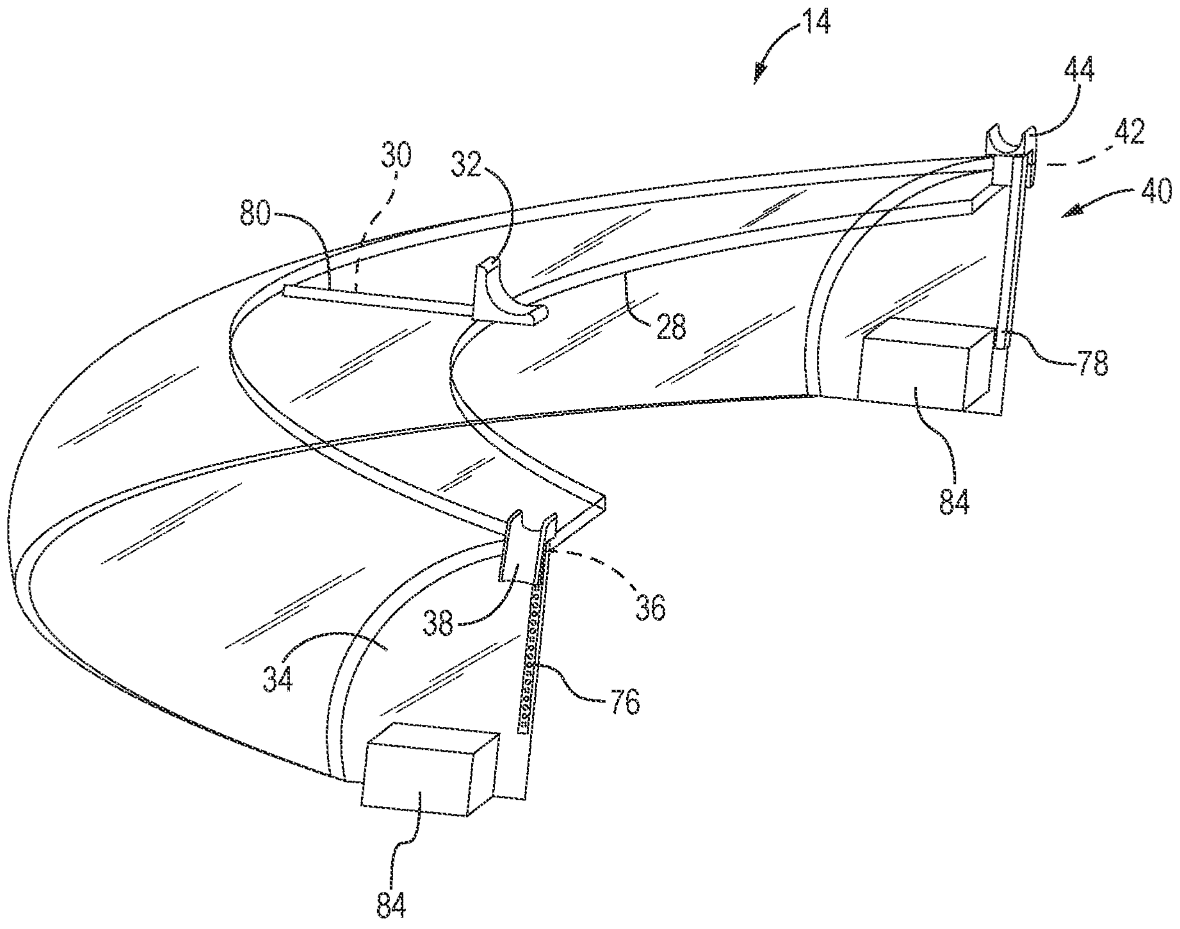
FIG. 8 is a detailed perspective view of a cannula support assemblage as in FIG. 2.

FIG. 8 most clearly shows exemplary features of the cannula support top 14 introduced above. More particularly, the receiver 30 is formed approximately at a midpoint of the ventilation director 28 to receive an arm 80 of the nose cannula cradle 32 for supporting a portion of the cannula 3 (compare FIG. 4). Also shown is the first end 34 with its first receiver 36 for receiving an arm 76 of the first cannula support 38 to cradle another portion of the cannula 3. And the second end 40 of the cannula support top 14 includes the second receiver 42 receiving an arm 78 of the second cannula support 44 to cradle a further portion of the cannula 3. As shown by way of example on the arm 76, arms 76, 78, and 80 may include raised areas or bumps that press fit into their respective receivers 30, 36, and 40 to secure the cradles 32, 38, and 44 in place. Further, the ventilation director 28 in conjunction with the spacers 84 as explained below cooperate to direct exhalations away from a face of the user.

Figure 9:
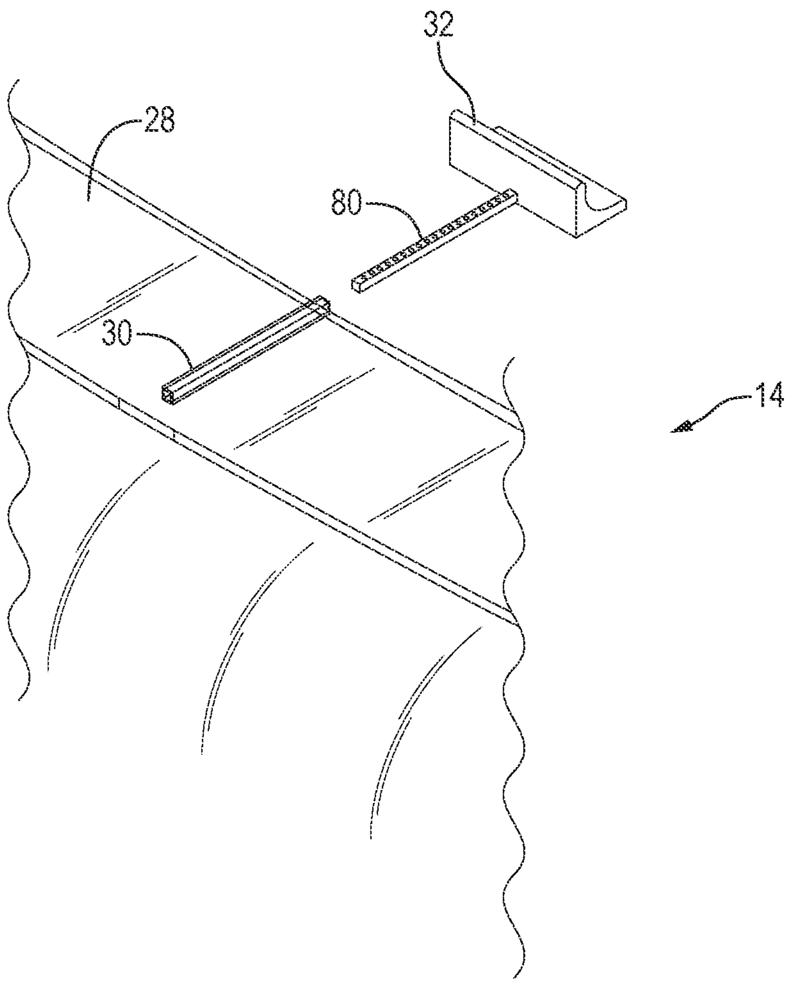
FIG. 9 is an exploded, partial, perspective view of a midpoint receiver for a nose portion of a cannula as in FIG. 8.
Figure 10:
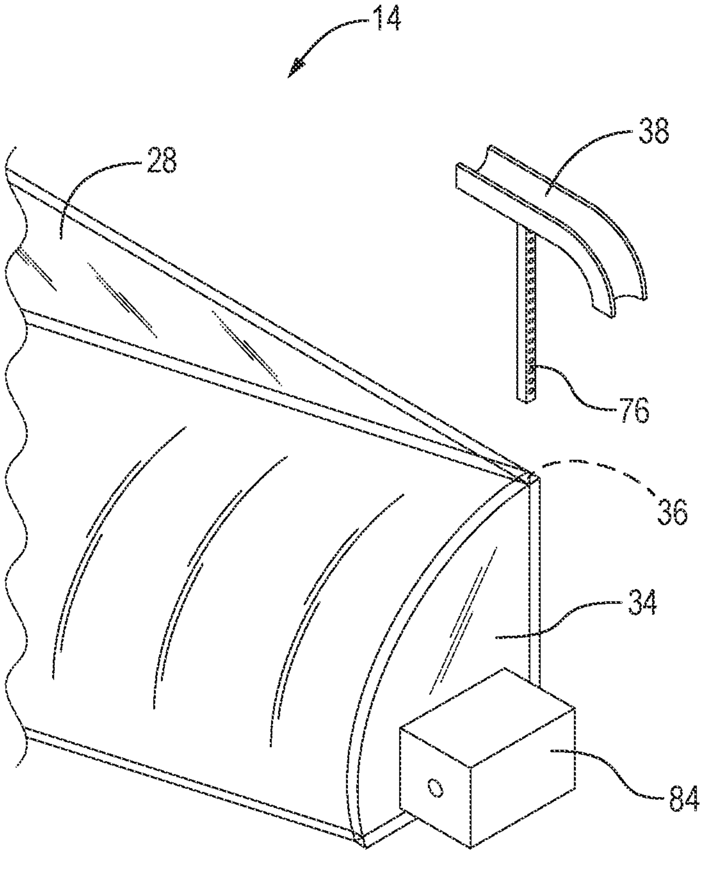
FIG. 10 is an exploded, partial, perspective view of an end receiver for a side portion of a cannula as in FIG. 8.

FIG. 9 most clearly shows the arm 80 of the cradle 32 readied for press fitting into the receiver 30, which is formed along the cannula support top 14 for securing the cannula cradle 32 in place. Similarly, in FIG. 10 the arm 76 of the cradle 38 is shown readied for press fitting into the receiver 36, which is formed at the first end 34 of the cannula support top 14 for securing the cradle 38 in place. As noted above, the spacer 84 will be used to position the clip 26 (see, e.g., FIG. 6).

Figure 11:
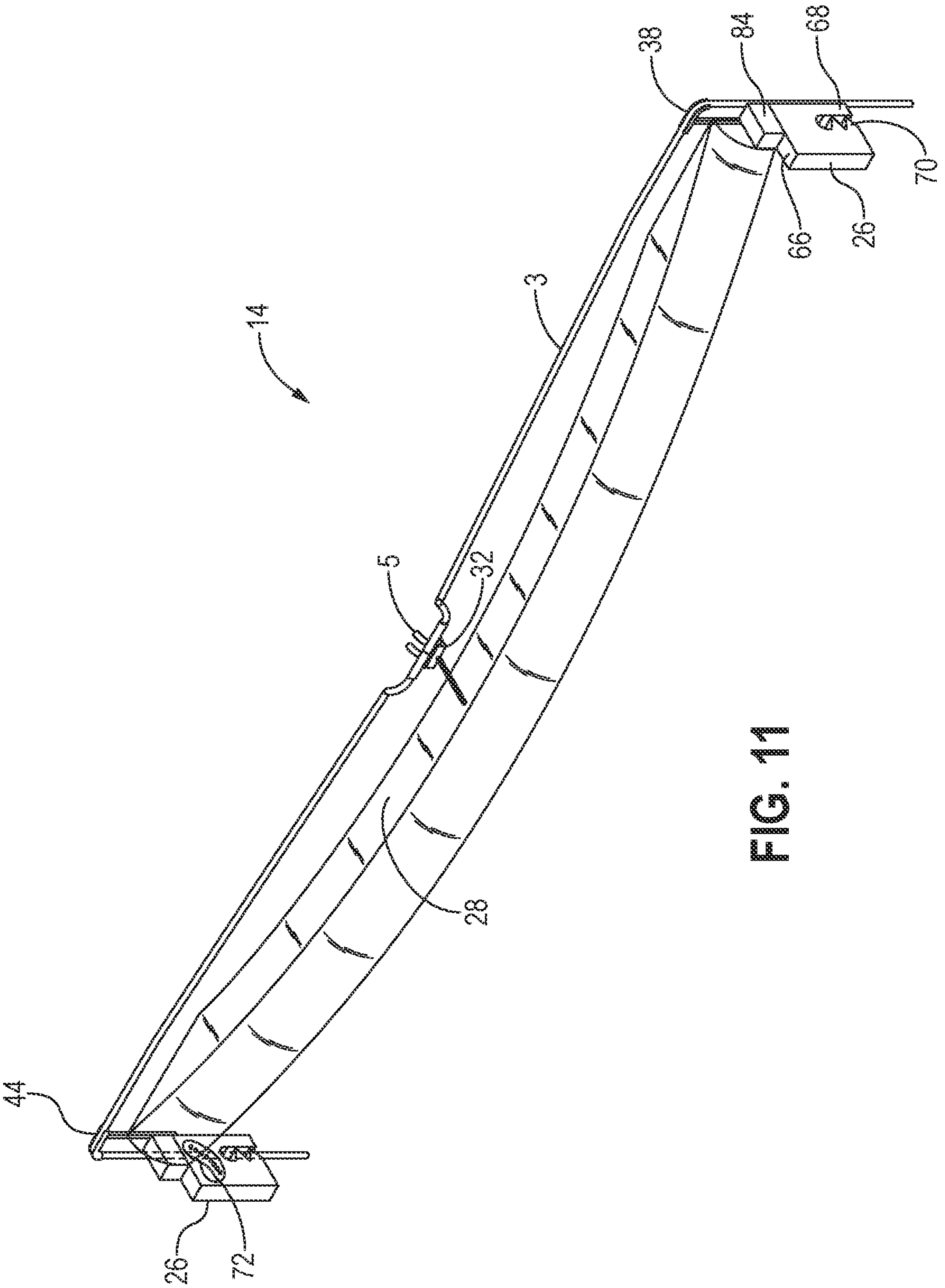
FIG. 11 is a partial perspective view of the cannula support assemblage as in FIG. 8, particularly showing a cannula arranged thereon.

FIG. 11 is a perspective view of the cannula support top 14 in which portions of the cannula 3 are positioned in the nose cannula cradle 32, the first cannula support 38, and the second cannula support 44. Here, nose prongs 5 of the cannula 3 are most clearly shown extending from the nose cannula cradle 32 with the ventilation director 28 directing exhalations downward and away from the nose prongs 5. Also shown here are the clips 26 with their tops 66 positioned against the spacers 84 of the cannula support top 14. Further, the clips 26 may include swivel detents 72 for receiving respective swivels 24 of the face mask 12 (see FIG. 2).

Figure 12:
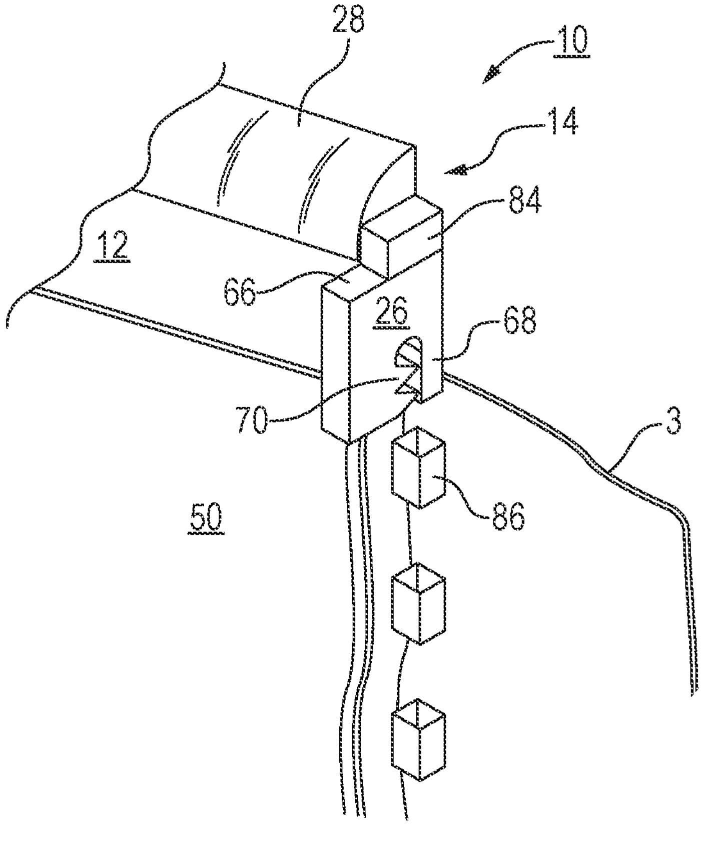
FIG. 12 is a partial perspective view of the cannula support assemblage as in FIG. 8, particularly showing a clip relative to receivers in the cloth portion of the mask system.
Figure 13:
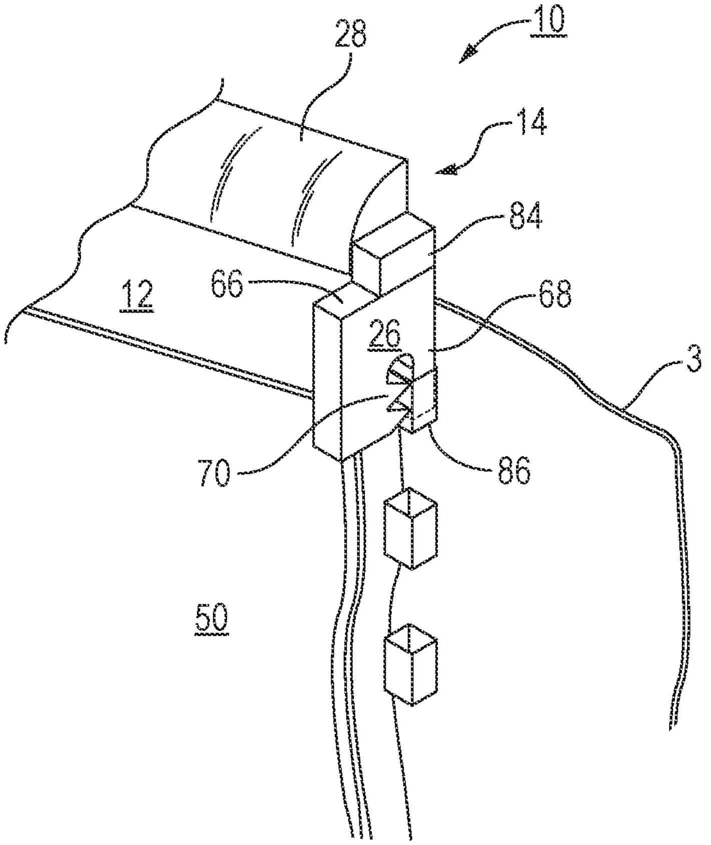
FIG. 13 is a partial perspective view of the cannula support assemblage as in FIG. 12, particularly showing the clip inserted in one of the receivers in the cloth portion.

FIGS. 12 and 13 show a portion of the mask assembly 10, particularly the interaction and connection of one of the clips 26 between the cannula support top 14 and an interior 50 of the cloth mask 16. More specifically, in FIG. 12 the clip 26 has been attached to the mask 12 at one end of the cannula support top 14 and its air deflector 28. The top 66 of the clip 26 is pressed against or has received the spacer 84 with the clip 26 positioned for insertion of the arm 68 into one of the clip holders or receivers 86 located in the interior 50 of the cloth mask 16. FIG. 13 shows the arm 68 inserted into the clip holder 86 which is gripped by the teeth 70 of the clip 26. The clip 26 may be formed with a spring constant provided between the arm 68 and the teeth 70 to assist in gripping the clip holder 86. If a user desires that the mask 12 sit lower in the cloth mask 16, perhaps to make additional room for the cannula 3, the clip 26 can be inserted into a different clip holder 86 as shown.

Figure 14:
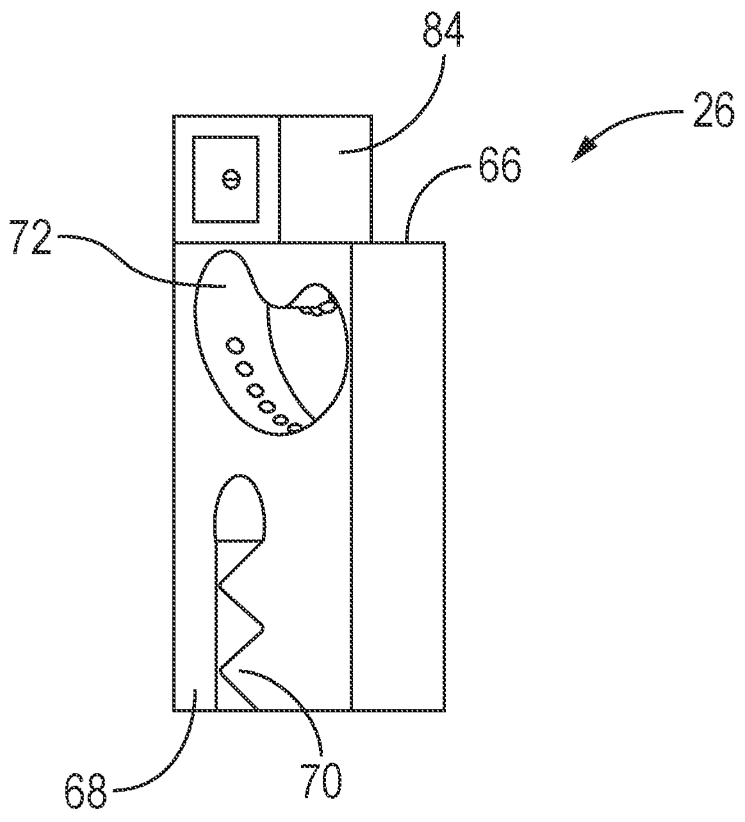
FIG. 14 is detailed inner perspective view of the exemplary clip as in FIG. 7, particularly showing a swivel receiver and a spacer of the cannula support assemblage in a first position.
Figure 15:
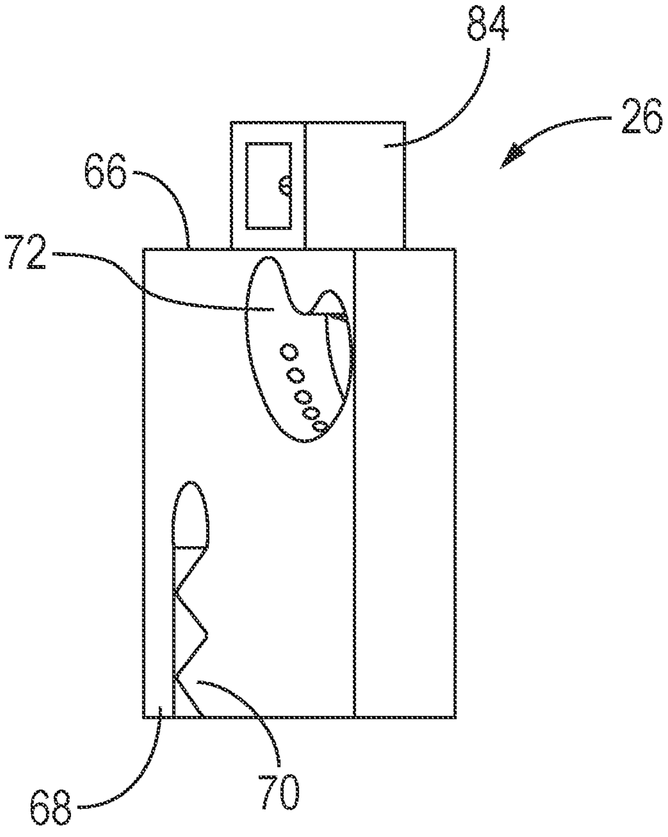
FIG. 15 is detailed inner perspective view of the exemplary clip similar to FIG. 14, particularly showing the spacer in a second position.

With reference now to FIGS. 14 and 15, an interior side of the clip 26 is most clearly shown (compare FIGS. 6 and 7). FIG. 14 shows the swivel detents 72 for receiving respective swivels 24 of the face mask 12 (see FIG. 2), as well as the arm 68 and the teeth 70 to assist in gripping the clip holder 86 as discussed above with regard to FIG. 13. But more particularly, the spacer 84 in FIG. 14 is shown inserted into the top 66 of the clip 26 such that the cannula support top 14 is, for instance, closest to a face of a user. By comparison, the spacer 84 in FIG. 15 is shown placed approximately in a middle of the top 66 of the clip 26 such that the cannula support top 14 will be approximately one quarter of an inch (¼ in.) farther away from the user face.

By way of example and not of limitation, various embodiments according to the disclosure may include:

EMBODIMENT 1: A reusable mask system comprising a swivable shield having a first side with a first swivel depending therefrom and a second side with a second swivel depending therefrom; a mask having an external layer and an internal layer forming a pocket therebetween, the swivable shield being insertable in the pocket; a cannula support assemblage having a first assemblage end and a second assemblage end and further including a ventilation director and a nose cradle depending from the ventilation director, the nose cradle being configured for supporting a cannula; a first clip attachable to the first assemblage end and configured to receive the first swivel of the swivable shield; and a second clip attachable to the second assemblage end and configured to receive the second swivel of the swivable shield.

EMBODIMENT 2: The reusable mask system as in Embodiment 1, wherein the swivable shield is made of a synthetic resin.

EMBODIMENT 3: The reusable mask system as in Embodiments 1 or 2, wherein the internal layer of the mask is made of woven fabric.

EMBODIMENT 4: The reusable mask system as in any of the foregoing embodiments, wherein the ventilation director is spaced apart from the internal layer and is configured to deflect exhalations away from the cannula.

EMBODIMENT 5: The reusable mask system as in any of the foregoing embodiments, wherein the first clip and the second clip are horizontally adjustable.

EMBODIMENT 6: The reusable mask system as in any of the foregoing embodiments, further comprising a cannula support disposed at a first assemblage end or a second assemblage end for supporting a portion of the cannula.

EMBODIMENT 7: The reusable mask system as in any of the foregoing embodiments, further comprising a nose segment connectable to one of the cannula support assemblage or the mask, the nose segment configured to provide a nose cushion.

EMBODIMENT 8: The reusable mask system as in any of the foregoing embodiments, further comprising wherein a nose bridge connectable to one of the cannula support assemblage or the mask to fit the cannula support assemblage or the mask to a user, the nose bridge being malleable for user fitment.

EMBODIMENT 9: The reusable mask system as in any of the foregoing embodiments, further comprising receivers disposed in the pocket to receive respective clips.

EMBODIMENT 10: A reusable mask system, comprising a shield having a swivel depending therefrom; a mask having an external layer and an internal layer forming a pocket therebetween, the shield being insertable in the pocket; a cannula support top disposed on the mask, the cannula support top being configured to support a portion of a cannula; and a clip attachable to the cannula support top configured to receive the swivel.

EMBODIMENT 11: The reusable mask system as in Embodiment 10, wherein the clip is horizontally adjustable.

EMBODIMENT 12: The reusable mask system as in Embodiments 10 or 11, wherein the cannula support top includes an assemblage end and further comprising a shoulder support depending from the assemblage end for supporting another portion of the cannula.

EMBODIMENT 13: The reusable mask system as in Embodiments 10, 11, or 12, further comprising a ventilation deflector spaced apart from the internal layer and configured to deflect exhalations away from the cannula.

EMBODIMENT 14: The reusable mask system as in any of Embodiments 10 through 13, further comprising a nose cradle depending from the cannula support top and being configured for supporting another portion of the cannula.

EMBODIMENT 15: The reusable mask system as in any of Embodiments 10 through 14, further comprising a nose segment connectable to one of the cannula support top or the mask, the nose segment configured to provide cushioning.

EMBODIMENT 16: The reusable mask system as in any of Embodiments 10 through 15, further comprising a nose bridge connectable to one of the cannula support assemblage or the mask to fit the cannula support assemblage or the mask to a user, the nose bridge being malleable for user fitment.

EMBODIMENT 17: The reusable mask system as in any of Embodiments 10 through 16, further comprising receivers disposed in the pocket to receive respective clips.

EMBODIMENT 18: A reusable mask system, comprising a swivelable facial shield and a cannula support assemblage disposed proximate the shield, the cannula support assemblage having a first end and a second end with a first shoulder support depending from the first end and a second shoulder support depending from the second end, and further including a ventilation director and a nose cradle depending from the ventilation director, the first and second shoulder supports and the nose cradle being configured for supporting a cannula.

EMBODIMENT 19: The reusable mask system as in Embodiment 18, further comprising a mask having an external layer and an internal layer forming a pocket therebetween, the shield being insertable in the pocket.

EMBODIMENT 20: The reusable mask system as in Embodiments 18 or 19, further comprising receivers disposed in the pocket to receive the shield.

While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

That which is claimed is:

1. A reusable mask system, comprising:

a swivable shield having a first side with a first swivel depending therefrom and a second side with a second swivel depending therefrom;

a mask having an external layer and an internal layer forming a pocket therebetween, the swivable shield being insertable in the pocket;

a cannula support assemblage having a first assemblage end and a second assemblage end and further including a ventilation director and a nose cradle depending from the ventilation director, the nose cradle being configured for supporting a cannula;

a first clip attachable to the first assemblage end and configured to receive the first swivel of the swivable shield; and a second clip attachable to the second assemblage end and configured to receive the second swivel of the swivable shield.

2. The reusable mask system as in claim 1, wherein the swivable shield is made of a synthetic resin.

3. The reusable mask system as in claim 1, wherein the internal layer of the mask is made of woven fabric.

4. The reusable mask system as in claim 1, wherein the ventilation director is spaced apart from the internal layer and is configured to deflect exhalations away from the cannula.

5. The reusable mask system as in claim 1, wherein the first clip and the second clip are horizontally adjustable.

6. The reusable mask system as in claim 1, further comprising a cannula support disposed at a first assemblage end or a second assemblage end for supporting a portion of the cannula.

7. The reusable mask system as in claim 1, further comprising a nose segment connectable to one of the cannula support assemblage or the mask, the nose segment configured to provide a nose cushion.

8. The reusable mask system as in claim 1, further comprising a nose bridge connectable to one of the cannula support assemblage or the mask to fit the cannula support assemblage or the mask to a user, the nose bridge being malleable for user fitment.

9. The reusable mask system as in claim 1, further comprising receivers disposed in the pocket to receive respective clips.

10. A reusable mask system, comprising:

a shield having a swivel depending therefrom;

a mask having an external layer and an internal layer forming a pocket therebetween, the shield being insertable in the pocket;

a cannula support top disposed on the mask, the cannula support top being configured to support a portion of a cannula; and a clip attachable to the cannula support top configured to receive the swivel.

11. The reusable mask system as in claim 10, wherein the clip is horizontally adjustable.

12. The reusable mask system as in claim 10, wherein the cannula support top includes an assemblage end and further comprising a shoulder support depending from the assemblage end for supporting another portion of the cannula.

13. The reusable mask system as in claim 10, further comprising a ventilation deflector spaced apart from the internal layer and configured to deflect exhalations away from the cannula.

14. The reusable mask system as in claim 10, further comprising a nose cradle depending from the cannula support top and being configured for supporting another portion of the cannula.

15. The reusable mask system as in claim 10, further comprising a nose segment connectable to one of the cannula support top or the mask, the nose segment configured to provide cushioning.

16. The reusable mask system as in claim 10, further comprising a nose bridge connectable to one of the cannula support assemblage or the mask to fit the cannula support assemblage or the mask to a user, the nose bridge being malleable for user fitment.

17. The reusable mask system as in claim 10, further comprising receivers disposed in the pocket to receive respective clips.

18. A reusable mask system, comprising:

a swivelable facial shield; and a cannula support assemblage disposed proximate the shield, the cannula support assemblage having a first end and a second end with a first shoulder support depending from the first end and a second shoulder support depending from the second end, and further including a ventilation director and a nose cradle depending from the ventilation director, the first and second shoulder supports and the nose cradle being configured for supporting a cannula.

19. The reusable mask system as in claim 18, further comprising a mask having an external layer and an internal layer forming a pocket therebetween, the shield being insertable in the pocket.

20. The reusable mask system as in claim 19, further comprising receivers disposed in the pocket to receive the shield.

* * * * *